United States Patent [19]

Farer et al.

[11] Patent Number: 5,206,012
[45] Date of Patent: Apr. 27, 1993

[54] COMBINATION OF HOLLOW MICROSPHERES OF A THERMOPLASTIC SYNTHETIC MATERIAL, HEXAGONAL BORON NITRIDE AND N-ACYL LYSINE AS A HOMOGENIZATION AGENT FOR COSMETIC COMPACTED POWDERS

[75] Inventors: Alan M. Farer, Morganville; Fifi Hanna, Kearny; Elisa L. Fox, Upper Montclair; A. John Penicnak, Mountain Lakes, all of N.J.

[73] Assignee: L'Oreal, Paris, France

[21] Appl. No.: 660,612

[22] Filed: Feb. 27, 1991

[30] Foreign Application Priority Data

Feb. 28, 1990 [FR] France ................. 90 02508

[51] Int. Cl.$^5$ .............................................. A61K 7/035
[52] U.S. Cl. ........................................ 424/69; 424/63; 424/489
[58] Field of Search ............ 424/69, 64, 65, 489, 424/63; 524/504; 428/405; 423/290

[56] References Cited

U.S. PATENT DOCUMENTS

| 4,640,943 | 2/1987 | Meguro et al. | 424/69 |
| 4,784,978 | 11/1988 | Ogasawara et al. | 423/290 |
| 4,837,011 | 6/1989 | Macchio et al. | 424/69 |
| 4,944,937 | 7/1990 | McCall | 424/65 |
| 4,983,663 | 1/1991 | Orikasa et al. | 524/504 |
| 4,994,264 | 2/1991 | Verdon et al. | 424/63 |
| 5,035,885 | 7/1991 | Arraudeau et al. | 424/69 |
| 5,073,364 | 12/1991 | Giezendanner et al. | 424/69 |

FOREIGN PATENT DOCUMENTS 0139481  5/1985  European Pat. Off. .
0254612  1/1988  European Pat. Off. .

Primary Examiner—Thurman K. Page
Assistant Examiner—D. Colucci
Attorney, Agent, or Firm—Cushman, Darby & Cushman

[57] ABSTRACT

A cosmetic ingredient homogenization agent, for use in assisting and improving the homogenization of the cosmetic ingredients of a compacted powder, is a combination of the following three components: x weight percent of hollow microspheres of a thermoplastic synthetic material having a specific mass lower than 0.1 g/cm$^3$ and having a size lower than 30 μm; y weight percent of particles of hexagonal boron nitride; and z weight percent of particles of N-acyl lysine. x, y and z are numbers which vary, respectively, as follows: x: 0.2-30; y: 02.-90; and z: 8-99.78. The sum x+y+z=100. This homogenization agent can be incorporated into a cosmetic composition in the form of a compacted powder in an amount ranging from 1-55, preferably 10-35, percent by weight based on the total weight of the composition.

7 Claims, No Drawings

COMBINATION OF HOLLOW MICROSPHERES OF A THERMOPLASTIC SYNTHETIC MATERIAL, HEXAGONAL BORON NITRIDE AND N-ACYL LYSINE AS A HOMOGENIZATION AGENT FOR COSMETIC COMPACTED POWDERS

The invention relates to a cosmetic ingredient homogenization agent for use in the preparation of a cosmetic composition in the form of a compacted powder. This homogenization agent consists of a ternary combination of components which assists and improves the homogenization of the ingredients of the cosmetic compacted powder composition. Specifically this homogenization agent consists of a combination of a thermoplastic synthetic material in the form of hollow microspheres, hexagonal boron nitride particles and an acylated derivative of lysine.

It is known that known cosmetic compositions in the form of powders include numerous ingredients. Their production requires mixing, grinding and sifting operations which are relatively long and energy costly.

These operations are even more delicate in the preparation of compacted powders, which operations generally include the addition, for example, by pulverization, of an oily phase, to a particulate mixture of the other ingredients which make up the compacted powder. Techniques to distribute the oily phase as uniformly as possible and to ultimately homogenize the product after the addition of the oily phase, are particularly time consuming and difficult operations.

The present invention provides a remedy for these disadvantages, thanks to the use, in combination, of hollow microspheres of a thermoplastic synthetic material, hexagonal boron nitride particles and an N-acylated derivative of lysine. Such a combination imparts to the mass of particles, during preparation of the compacted powder, an exceptional fluidity and permits then to reduce production costs in terms of time and energy. Moreover, this combination permits to obtain compacted powders of high quality, having satisfactory properties of compactness and shock resistance, while having pleasing application characteristics.

The use of hollow microspheres of a thermoplastic synthetic material, in free non-compacted powders for makeup and the care of skin, has already been described, and principally in French patent No.86 09289 (publication No. 2600532). The use of hollow microspheres in cosmetic composition powder form has also been described in Japanese patent application 60-18404. However, the hollow microspheres specifically employed, according to this Japanese patent application, have a relatively high specific mass and are thus not appropriate for implementing the present invention.

The use of hexagonal boron nitride particles in cosmetic compositions in powder form has been described in Japanese patent application 62.49247.

The use of talc coated with an acylamino acid in a cosmetic composition, in powder form, containing silica, mica, polyethylene and a particular binder including a combination of polydimethylsiloxane, distearyl malate and pentahydrosqualene has been described in U.S. Pat. No. 4,837,011.

It has now been discovered that the combination of the three ingredients mentioned above impart to the particulate mixture employed in the preparation of a compacted powder fluidity which is quite superior to that obtained with the ingredients employed up to the present.

The present invention thus relates to the use, in the preparation of a cosmetic composition in the form of a compacted powder, from 1-55 weight percent, relative to the total weight of the cosmetic compacted composition, of a combination of three components which assists and improves the homogenization of the ingredients making up the cosmetic compacted powder composition, to wit:

x weight percent of hollow microspheres of a thermoplastic synthetic material having a specific mass lower than 0.1 g/cm$^3$ and having a size less than 30 µm, y weight percent of hexagonal boron nitride particles and z weight percent of N-acyl lysine particles, x, y and z being numbers varying respectively in the following ranges:

x : 0.2-30,
y : 0.2-90 and
z : 8 to 99.78
it being understood that $x+y+z=100$.

It is necessary to note that the x, y and z amounts are amounts relative to the three constituents in combination and not the amounts of these three constituents in the cosmetic composition which contains however, other than the three constituents in combination, various components usually present in compositions in the form of compacted powders.

In particular embodiments of the present invention, the ternary combination mentioned above can also exhibit the following characteristics, taken singly or in combination:

x is a number ranging from 0.5 to 2;
y is a number ranging from 5 to 25;
z is a number ranging from 75 to 95; and
the hollow microspheres have a size ranging from about 10 to 20 µm.

The three components in combination, defined above, represent preferably from 10 to 35 weight percent of the cosmetic compacted powder composition based on the total weight of the said cosmetic composition.

The hollow microspheres are prepared in accordance with known procedures, such as those described in U.S. Pat. No. 3,615,972 and European Patent No. 0 056 219.

The hollow portion of the microspheres contains a gas such as a hydrocarbon (butane, pentane), air or any other conventionally employed gas.

These microspheres can be produced from any non-toxic and non-irritating thermoplastic material. This material can be, for example, polymers or copolymers of ethylenic derivatives (for example, polyethylene, polystyrene, vinyl chloride-acrylonitrile copolymer, etc.), polyamides, polyesters, urea-formaldehyde polymers, vinylidene chloride copolymers (for example, vinylidene chloride-acrylonitrile), etc.

The specific mass of the hollow microspheres is preferably in the order of 0.01 to 0.1 g/cm$^3$.

The hexagonal boron nitride particles preferably have a size ranging from 0.1 to 30 µm.

Representative hollow microspheres, employed in the composition of the present invention, include principally, those sold under the tradename EXPANCEL 551 DE 20 (size: 20 µm) and 55 DE 12 (size: 12 µm) by Kemanord Plant.

The N-acyl lysine particles preferably have a size ranging from 5 to 30 µm. Representative N-acylated lysine derivatives include, in particular, those whose acyl group is derived from a fatty acid having 8 to 18 carbon atoms. A preferred N-acylated lysine derivative is, principally, N-lauroyl lysine.

The present invention also relates to a cosmetic composition in the form of a compacted powder comprising from 1 to 55 weight percent and preferably from 10 to 35 weight percent, of the ternary combination, such as defined above.

The composition of the present invention also contains charges or fillers and/or conventional pigments as well as an oily phase.

The pigments and/or charges are those conventionally employed in cosmetic compositions in the form of compacted powders. The pigments are selected principally from mineral pigments, organic pigments and nacreous pigments.

Representative mineral pigments, include, for example: titanium dioxide (rutile or anatase) optionally surface treated and listed in the Color Index under reference CI 77891; black, yellow, red and brown iron oxides listed in Color Index under references CI 77499, 77492 and 77491;
   manganese violet (CI 77742);
   ultramarine blue (CI 77007);
   chromium oxide (CI 77288);
   hydrated chromium oxide (CI 77289);
   ferric blue (CI 77510).

Representative the organic pigments include, in particular, the following:
   D & C Red No. 19 (CI 45170;
   D & C Red No. 9 (CI 15585);
   D & C Red No. 21 (CI 45380);
   D & C Orange No. 4 (CI 15510);
   D & C Orange No. 5 (CI 45370);
   D & C Red No. 27 (CI 45410);
   D & C Red No. 13 (CI 15630);
   D & C Red No. 7 (CI 15850:1);
   D & C Red No. 6 (CI 15850:2);
   D & C Yellow No. 5 (CI 19140);
   D & C Red No. 36 (CI 12085);
   D & C Orange No. 10 (CI 45475);
   D & C Yellow No. 6 (CI 15985);
   D & C Red No. 30 (CI 73360);
   D & C Red No. 3 (CI 45430);
   carbon black (CI 77766); and
   carmine lakes (CI 75470).

The nacreous pigments can be selected principally from:
   white nacreous pigments such as mica covered with titanium oxide, bismuth oxychloride; and
   colored nacreous pigments, such as titanium mica with iron oxides, titanium mica with ferric blue or chromium oxide, titanium mica with an organic pigment of the aforementioned type, as well as those based on bismuth oxychloride.

These pigments can represent, preferably, from 0.1 to 2 weight percent based on the total weight of the cosmetic compacted powder composition.

The charges or fillers are selected principally from:
   micas which are aluminosilicates of varied compositions, and which are provided in the form of flakes having a size ranging from 2 to 200 $\mu$m, preferably from 5 to 70 $\mu$m and a thickness from 0.1 to 5 $\mu$m, preferably from 0.2 to 3 $\mu$m. The micas can be of natural origin (for example, muscovite, margarite, rescolithe, lipidolithe, biotite), or of synthetic origin. The micas are generally transparent and impart to the skin a satin aspect. Generally, in the cosmetic compositions of the present invention, the micas represent from 20 to 70 weight percent and preferably from 30 to 50 weight percent based on the total weight of the cosmetic composition;
   magnesium carbonate or bicarbonate, which possesses principally perfume fixing characteristics; they can be present, in the cosmetic composition of the present invention, in an amount ranging from 1 to 10 weight percent, preferably from 2 to 7 weight percent based on the total weight of the cosmetic composition;
   metallic soaps derived from organic carboxylic acids having from 8 to 22 carbon atoms, preferably from 12 to 18 carbon atoms, for example, zinc stearate, magnesium stearate, lithium stearate, zinc laurate, magnesium myristate, etc. These soaps, present generally in the form of particles having a size less than 10 $\mu$m, have an unctuous feel and facilitate the adherence of the powder to the skin. These metallic soaps are generally present in an amount ranging from 1 to 10 weight percent, preferably from 2 to 7 weight percent based on the total weight of the composition;
   synthetic polymer powders, such as polyethylene, polyesters (for example polyethylene isophthalate or terephthalate) and polyamides (for example, nylon), under the form of particles having a size less than 50 $\mu$m, which possess absorbing properties so as to impart to the skin a velvety appearance; these synthetic polymer powders are present in the cosmetic composition of the present invention in an amount ranging from 1 to 40 weight percent, preferably from 10 to 30 weight percent, based on the total weight of the cosmetic composition.

The cosmetic compacted powder composition of the present invention can also contain other charges or fillers such as talc, starch, kaolin, zinc and titanium oxides, precipitated calcium carbonate, etc.

The fatty phase generally includes fatty bodies which are liquid at ambient temperature and which are present in the cosmetic composition in amounts ranging from 2 to 10 weight percent, preferably 4 to 8 weight percent based on the total weight of the cosmetic composition.

Representative fatty bodies liquid at ambient temperature, include mineral, animal, vegetable or synthetic oils, or silicone oils. Specific examples include the following oils: petrolatum oil, liquid lanolin, arara oil, sesame oil, macadamia oil or jojoba oil, and synthetic triglycerides.

The fatty phase can also contain an oleosoluble synthetic polymer whose use in cosmetic compositions is known.

Representative oleosoluble synthetic polymers include polyvinylpyrrolidone/hexadecene or PVP/eicosene copolymers, such as products sold by GAF Corp. under the tradename "GANEX V-216" and "GANEX V-220".

The added optional fatty phase represents 0 to 25 weight percent, preferably 3 to 20 weight percent, based on the total weight of the cosmetic composition.

Other various ingredients can be included in the compacted composition such as antiseptic agents (trichloro diphenyl ether, cationic agents, boric acid, etc.), which are employed principally in deodorizing powders for the body and feet and in baby powders; astringent agents, which are used in deodorizing powders or in foot powders, such as aluminum hydroxychloride or alums; sunscreen agents; softening agents; hydrating agents (sorbitol, glycerine); cicatrisive agents; anti-free radical agents; vitamins; perfumes, etc.

These ingredients can represent up to 5 weight percent based on the total weight of the cosmetic composition.

Finally, the compacted powders in accordance with the present invention optionally contain hydrosoluble stability agents (up to 20 weight percent), such as natural or synthetic gums, cellulose derivatives or acrylic polymers.

The compacted powders of the present invention are prepared in accordance with known techniques for the preparation of compacted powders. Generally the following procedures are carried out: the particulate constituents, defined above, are admixed and homogenized. Moreover an oily phase is prepared which contains the preservatives and optionally perfume. The oily phase is pulverized with the particulate phase, all while mixing. The resulting powder is distributed into appropriate containers and the powder is pressed in a conventional manner at a pressure sufficient to obtain a compacted powder having the desired degree of compactness.

The following non-limiting example illustrates the present invention.

EXAMPLE

A compacted powder is prepared having the following composition:

| Particulate ingredients | Weight percent |
| --- | --- |
| Mica (Sericite S 152; Presperse, Inc. | 44 |
| Nylon powder (Orgasol 2002 D-Extra; Lipo Chemical Co.) | 25 |
| N-lauroyl lysine (Amihope LL; Centerchem) | 15 |
| Zinc stearate | 1 |
| Magnesium carbonate | 2 |
| Hexagonal boron nitride | 3 |
| Hollow microspheres (Expancel 551DE20) | 0.25 |
| Pigments | 1.5 |
| Oily Phase | |
| Octadodecyl stearate (Ceraphyl 847, Malinckrödt Inc.) Dioctyl maleate Diisostearyl malate | 8 |
| Preservative | 0.125 |
| Perfume | 0.125 |
| Total | 100.00 |

We claim:

1. A homogenization agent for use in the preparation of a cosmetic powder composition in pressed or compact form so as to impart fluidity to said cosmetic powder composition, said homogenization agent consisting of a combination of three components which assist and improve the homogenization of the particulate ingredients of said cosmetic powder composition, said three components being;

x weight percent of hollow microspheres of a thermoplastic non-toxic and nonirritating synthetic polymeric material having a specific mass lower than 0.1 g/cm$^3$ and having a size lower than 30 $\mu$m and being selected from the group consisting of an ethylenic hydrocarbon, a polyester, a polyamide, a urea formaldehyde polymer and a copolymer of vinylidene chloride, y weight percent of particles of hexagonal boron nitride, and z weight percent of N-acyl lysine wherein the acyl moiety has 8 to 18 carbon atoms, wherein x, y and z are numbers varying, respectively, in the following ranges:

x: 0.2–30,
   y: 0.2–90,
   z: 8–99.78 and wherein the sum of $x+y+z=100$.

2. The homogenization agent of claim 1 wherein x is a number ranging from 0.5 to 2.

3. The homogenization agent of claim 1 wherein y is a number ranging from 5 to 25.

4. The homogenization agent of claim 1 wherein z is a number ranging from 75 to 95.

5. The homogenization agent of claim 1 wherein said acyl is lauroyl.

6. A cosmetic composition in the form of a compacted powder comprising 1–55 weight percent of a cosmetic ingredient homogenization agent, said homogenization agent consisting of a combination of three components which assist and improve the homogenization of the ingredients of said cosmetic composition, said three components being:

x weight percent of hollow microspheres of a thermoplastic synthetic material having a specific mass lower than 0.1 g/cm$^3$ and having a size lower than 30 $\mu$m, y weight percent of particles of hexagonal boron nitride, and z weight percent of particles of N-acyl lysine, wherein x, y and z are numbers varying, respectively, in the following ranges:

x: 0.2–30,
   y: 0.2–90,
   z: 8–99.78 and wherein the sum, $x+y+z=100$.

7. The cosmetic composition of claim 6 wherein said cosmetic ingredient homogenization agent is present in an amount ranging from 10 to 35 weight percent based on the total weight of said cosmetic composition.

* * * * *